United States Patent [19]

Chan

[11] Patent Number: 4,477,685

[45] Date of Patent: Oct. 16, 1984

[54] HYDROFORMYLATION PROCESS TO PREPARE GLYCOLALDEHYDES

[75] Inventor: Albert S. Chan, St. Charles, Mo.

[73] Assignee: Monsanto Company, St. Louis, Mo.

[21] Appl. No.: 409,819

[22] Filed: Aug. 20, 1982

[51] Int. Cl.³ .............................................. C07C 45/49
[52] U.S. Cl. .................................... 568/462; 568/458; 568/465
[58] Field of Search .................... 568/462, 465, 458

[56] References Cited

U.S. PATENT DOCUMENTS

| | | | |
|---|---|---|---|
| 3,920,753 | 11/1975 | Yukawa t al. | 568/458 |
| 4,052,461 | 10/1977 | Tinker et al. | 568/454 |
| 4,200,765 | 4/1980 | Goetz | 568/462 |
| 4,238,418 | 12/1980 | Weiss | 568/458 |
| 4,405,814 | 9/1983 | Carroll et al. | 568/462 |

FOREIGN PATENT DOCUMENTS 7407544 12/1974 Netherlands ........................ 568/458

OTHER PUBLICATIONS

Miller et al., J. Chem. Physics, vol. 51, pp. 3185–3191.

*Primary Examiner*—Werren B. Lone
*Attorney, Agent, or Firm*—Joseph D. Kennedy; James W. Williams, Jr.

[57] ABSTRACT

Formaldehyde is reacted with hydrogen and carbon monoxide with rhodium catalyst in the presence of phosphine ligands having electron-withdrawing substituents, obtaining high selectivity to glycol aldehyde with a stable catalyst system.

17 Claims, No Drawings

HYDROFORMYLATION PROCESS TO PREPARE GLYCOLALDEHYDES

This invention relates to improvements in the production of glycol aldehyde by the reaction of formaldehyde, carbon monoxide and hydrogen in the presence of rhodium catalyst and certain phosphines.

BACKGROUND OF THE INVENTION

Glycol aldehyde is a valuable intermediate useful in the synthesis of other organic compounds, and can be converted, for example, to ethylene glycol by hydrogenation. Processes for the production of glycol aldehyde by the reaction of formaldehyde with carbon monoxide and hydrogen in the presence of certain rhodium catalysts are described in the co-pending application of Alwyn Spencer, Ser. No. 256,183 filed Apr. 21, 1981, assigned to the same assignee as the present application, and corresponding European Patent EP No. 0 002 908, and also in U.S. Pat. No. 4,200,765, issued to Richard W. Goetz on Apr. 29, 1980. Also, commonly assigned copending application Ser. No. 290,622 of the present applicant and another describes the use of amines as promoters for such reactions in which tertiary organo phosphorus or arsenic groups are present as modifying ligands in rhodium catalysts. The amines improve reaction rate and permit use of high phosphine or arsine to rhodium ratios, thereby improving catalyst stability, without the excessive loss of reaction rate which would otherwise occur.

SUMMARY OF THE INVENTION

The improved process of the present invention is carried out by reacting formaldehyde, carbon monoxide and hydrogen (under temperature and pressure conditions conducive to the formation of glycol aldehyde) in the presence of rhodium catalyst and a phosphine in which there is an electron-withdrawing substituent on an aryl ring of the phosphine. The presence of such phosphines contributes to better reaction rate and higher selectivity to glycol aldehyde, particularly when an excess of phosphine is employed to enhance catalyst stability. The electron-withdrawing substituent makes the phosphine less basic. The product produced in the present process contains very little glycol aldehyde condensation product, in contrast to the tendency of amine promoters to cause production of considerable condensation product. Suitably substituted triaryl phosphines are usefully employed, e.g. tris (4-trifluoromethylphenyl) phosphine.

DETAILED DESCRIPTION OF THE INVENTION

The rhodium catalyts used herein are comprised of a rhodium component in association with ligands, as described in detail in U.S. Pat. No. 4,052,461, issued to Harold B. Tinker and Donald E. Morris on Oct. 4, 1977 and the aforementioned U.S. patent application Ser. No. 256,183, both of which are hereby incorporated by reference in the present description. Generally, the rhodium component of such catalysts is considered to be present in the form of a coordination compound. Phosphines with electron-withdrawing substituents, as described herein, are generally a component of the active catalyst, whether provided to the reaction medium as part of a catalyst or catalyst precursor, or provided separately to the reaction medium. In addition to the rhodium component and phosphine, such coordination compound can include carbon monoxide (CO) ligands, hydride (H)ligands, halide or pseudo-halide components, or various other ligands. The term "coordination compound" as used herein means a compound or complex formed by a combination of one or more electronically rich molecules or atoms capable of independent existence with one or more electronically poor molecules or atoms, each of which may also be capable of independent existence. The rhodium may be complexed with from 3 to 6 or so ligands, and can be in a form usually considered as neutral or essentially nonvalent in common catalyst systems, or in cationic form as described in the aforesaid U.S. Pat. No. 4,052,461. The catalyst can be supplied to the reactants in active form or in the form of various catalyst precursors, and the catalyst also may undergo changes in the course of the reaction, or from the effect of the reaction conditions.

The substituted phosphines utilized in the present invention are characterized by having an electron withdrawing group substituted on an aryl ring of a phosphine. The electron-withdrawing group will ordinarily be in a position so as to have a strong effect upon a carbon-to-phosphorus bond of the phosphine, preferably in para-position of an aryl ring attached to phosphorus. One or more of the electron-withdrawing substitutents can be present in an aryl ring, but one effective group is sufficient so that there is ordinarily no need for more than one such group. The aryl rings can also contain other substituents, although strongly electron-donating groups should ordinarily be avoided. Triaryl phosphines with an electron-withdrawing group in para-position to the phosphorous are preferred. However, phosphines with substitution of electron-withdrawing groups in an aryl ring in ortho or meta positions can be employed, provided the substitution is effective to lower the basicity of the phosphine, making it less basic than triphenyl phosphine.

A number of electron-withdrawing groups are known to the art, e.g. trifluoromethyl, nitro, and cyano groups, and in general electron-withdrawing groups characterized by suitable Hammett values can be used. The substituents on the phosphorus of the phosphines can be the same or different, although it is generally more convenient for the groups to be the same. It is preferred that the aryl groups on which the electron-withdrawing groups are substituted be phenyl groups. Examples of phosphines with electron-withdrawing group substitution include tris(4-trifluoromethylphenyl)phosphine, tris(4-cyanophenyl) phosphine, tris(4-nitrophenyl) phosphine,tris(3-methyl-4-trifluoromethylphenyl) phosphine, tris(2-fluoro-4-trifluoromethyl-6-fluoromethylphenyl)phosphine, phenylbis-(trifluoromethylphenyl) phosphine, 4-cyanophenyl-bis(4-trifluoromethylphenyl) phosphine, etc. Aryl groups with acyl, e.g. —COOC$_2$H$_5$, groups can be used, although the carboxyalkyl or other ester groups may tend to be hydrolyzed and could interfere to some extent in the desired reaction. Aside from the required electron-withdrawing substituents on the aryl groups, it is convenient for the aryl groups on the phosphorus to be completely hydrocarbon, but other substituents can be present, particularly, non-interfering and relatively inert substituents such as fluorine atoms, for example. Phosphines with three substituted phenyl groups, P(C$_6$H$_4$X)$_3$, where X is an electron-withdrawing group, are convenient for use, and those with X in the para position are preferred.

In the present invention, it is desirable to employ strongly electron-withdrawing groups, such as those having $\sigma_p^o$ values of at least 0.4, with the $\sigma_p^o$ value being that from the Hammett equation.

The Hammett equation is:

$$\log \frac{k}{k_o} = \sigma\rho$$

and for $XC_6H_4$—

$k_o$ is the rate constant for X=H
k is the constant for the group X
$\rho$ is the constant for a given reaction under given conditions
$\sigma$ is a constant characteristic of X Hammett $\sigma$ values are available for various group substituted at the p or m positions of phenyl rings. A positive value of $\sigma$ indicates an electron withdrawing group, and such groups help reactions in which $\sigma$ is positive. The $\sigma_p^o$ value contemplates reactions at a site effectively insulated from $\pi$ electrons of the benzene rings. The Hammett equation and sigma values are discussed in "Advanced Organic Chemistry", Jerry March, 2nd Ed., McGraw-Hill, New York, N.Y., (1977), at pages 251–259, and $\sigma_p^o$ values are given in a table on page 256 which includes:

| Group | $\sigma_p^o$ |
|---|---|
| $CF_3$ | 0.54 |
| CN | 0.66 |
| $NO_2$ | 0.83 |
| $CH_3CO$ | 0.47 |

While the trifluoromethyl group is not as strongly electron-withdrawing as some other groups, aryl phosphines containing trifluoromethyl substituents can be conveniently prepared by a Grignard reaction, and the trifluoromethyl group is stable under reaction conditions. The cyano group is also relatively stable, but the nitro, group while effective, may tend to be used up under reaction conditions by reaction with carbon monoxide.

It is preferred that the electron-withdrawing group be in the para position of the aryl ring. However, such substituents in the meta or ortho positions still have some effect and are suitable for use as strongly electron-withdrawing groups in the present invention if the effect on basicity or related properties of phosphines with such substituents is equal to or greater than that of a para-substituted electron-withdrawing group with a $\sigma_p^o$ value of 0.4 or greater.

The substituted phosphines employed herein are either coordinated to the rhodium atom to form the coordination compound or complex, or present as the free compound, i.e. uncoordinated or uncomplexed, or in both forms, in the reaction solution containing the rhodium coordination complex. In the free compound state such compound has the potential to become coordinated to the rhodium atom via a ligand exchange reaction with a different ligand already coordinated to the rhodium atom.

Suitable organo phosphorus ligands which may comprise part of the ionic or neutral rhodium coordination compound used in this invention are those containing trivalent phosphorus and are referred to in this specification as phosphines. Phosphines are useful ligands in the present catalysts, and phosphines, without electron-withdrawing substituents as described herein, can be usefully employed as catalyst ligands herein without significant adverse effects in reaction rates if the amount of such phosphines is relatively low, such as not over 2 or 3 mols of such phosphine per rhodium atom. Thus, if desired, the catalyst can be provided to the reaction medium with ordinary triphenyl phosphine as a ligand, and then the excess phosphine for catalyst stabilizing purposes be that with electron-withdrawing substituents as described herein. Also, the small amount of phosphine coordinated with the rhodium can have substituents other than aryl groups on the phosphine, e.g. alkyl groups, but for the phosphine used in excess to have relatively less basic properties, it is appropriate to have only aryl groups on the phosphorus and to have electron-withdrawing substitution as described herein.

For phosphine ligands of the catalyst itself, organic radicals of any size and composition may be bonded to the phosphorous, and the radicals are preferably selected from the group consisting of aryl and alkyl groups. The more preferred ligands are those consisting of at least one but preferably two or three aryl groups as the organic moieties. For example, preferred modifying ligands are illustrated by the following structural formulae $PR_3$ where R is e.g. phenyl ($C_6H_5$—), or tolyl($CH_3C_6H_4$—), xylyl ($CH_3C_6H_3CH_3$), e.g. $P(C_6H_5)_3, P(CH_3C_6H_4)_3$.

The phosphine ligands, and, if desired, other ligands, satisfy the coordination number of the central rhodium atom, and thus form a rhodium-containing complex. The term coordination compound or coordination complex means a compound or complex formed by combination of one or more electronically rich molecules or atoms, e.g. triphenyphosphine, carbon monoxide, 1,5-cyclooctadiene, (herein referred to as COD), with one or more electronically poor molecules or atoms, e.g. rhodium.

The rhodium complexes used in the present invention are ionic or neutral compounds, with the ionic ones having a non-complexing anionic moiety and the neutral ones containing halide, pseudo halide or hydride moiety. These have the general formula $RhL_xAn$. In this formula, in the case of the ionic ones, rhodium moiety is $RhL_x^+$ and the non-coordinating anionic moiety $AN^-$ is exemplified by $BF_4^-$, $ClO_4^-$, $PF_6^-$, $NO_3^-$, and $SiF_6^{2-}$, and in the neutral ones An is halide, pseudo halide or hydride.

In the above formulae L is a ligand, (either the same or different ligands as described herein) and x varies from 2 to 5. The ligand L may or may not be a phosphine. For example, in the case where $[Rh(Ph_3P)_3]+$ is employed as the rhodium-containing cation, $Ph_3P$ is the ligand L. In the case where $[Rh(COD)(Ph_3P)_2]+$ is employed as the rhodium-containing cation, $Ph_3P$ and COD are the ligands L. In the case where $[Rh(COD)_2]+$ is employed as the rhodium-containing cation, COD is the ligand L, and an excess of tris(trifluorophenyl)phosphine or similar phosphine is furnished to the reaction solution. In cases where the ligand L is not a phosphine, it may be a ligand displaceable by carbon monoxide under reaction conditions, e.g. COD. Examples of the ligand L include:
mono-enes of 2 to 12 carbon atoms,
dienes of 4 to 12 carbon atoms,
trienes of 6 to 16 carbon atoms,
alkynes of 2 to 12 carbon atoms, ketones of 3 to 12 carbon atoms,
nitriles of 2 to 12 carbon atoms,
N-alkylamines of 2 to 12 carbon atoms,
N-N-dialkylamides of 3 to 12 carbon atoms,
sulfoxides of 1 to 12 carbon atoms,
tertiary organo phosphorus compounds of 3 to 90 carbon atoms,
tertiary organo arsenic compounds of 3 to 90 carbon atoms,
tertiary organo antimony compounds of 3 to 90 carbon atoms,
carbon monoxide and combinations thereof.

The ionic or neutral rhodium compounds described above are utilized in the present invention as a means of introducing rhodium into the reaction solution and are sometimes referred to as catalyst precursors. Other forms of rhodium may be used to form the rhodium catalyst, for example, rhodium metal or rhodium metal on carbon or rhodium halide may be introduced into the system to form the rhodium catalyst.

In general, the relatively less basic phosphines employed in the present invention can be used with any of the usual rhodium catalysts or catalyst precursors and their usual ligands. However, while the ordinary phosphines can be used as catalyst components in the present invention, they are not employed in excess to stabilize the catalyst, but any excess phosphines should be the relatively less basic phosphines as described herein. When phosphines, such as triphenyl phosphine, are employed as catalyst ligands in amounts up to about 2 mols per rhodium atom, the reactivity and selectivity to glycol aldehyde is fairly good, but catalyst stability tends to be poor. In the present invention relatively high excesses of the less basic phosphines can be present and good reaction rates and selectivity to glycol aldehyde are still obtained. In the present invention it will generally be desirable to employ more than 3 mols phosphine per rhodium atom, and may be advantageous to have 5 or more mols phosphine per rhodium atom; and it is feasible to use much larger amounts of phosphine, such as 10 or 20 mols phosphine per atom of rhodium, on up to 50 or more mols.

The present reaction can conveniently be effected in a solvent which favors the production of glycol aldehyde over that of methanol, which generally requires a polar solvent. Some amides have been found to be particularly useful as solvents in the present process and to favor production of glycol aldehyde over that of methanol, the amides being characterized by the absence of free hydrogen on the amido nitrogen atom. N,N-disubstituted amides, i.e. amides with two organo substituents, are useful, the amides being compounds characterized by

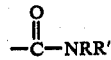

where R and R' are organo groups, and may usually be hydrocarbyl groups. The substituents on the nitrogen are often alkyl groups, particularly lower alkyl groups such as methyl, ethyl, propyl, butyl, pentyl, isopentyl, hexyl, etc. The amides are generally the amides of lower carboxylic acids, such as formic, acetic, propionic, hexanoic, etc. There is some variation in selectivity to glycol aldehyde with the variation in the chain length of the acid amide and the substituents on the nitrogen. The acetamides give particularly good results, but there is some loss in selectivity with increasing chain length of the nitrogen substituents on these and other amides. However another factor to be considered is suitability of the solvent for subsequent product separation procedures. Aqueous extractions may be employed, and a water immiscible reaction solvent is appropriate for such extraction procedure. The simple amides like dimethylformamide are water soluble but the amides tend toward water immiscibility with increasing chain length, particularly of hydrocarbon moieties, as with alkyl substituents on the nitrogen atom, and immiscibility is reached with sufficiently long chains. Thus di-n-butylformamide and di-isopentylformamide are suitable solvents for aqueous extraction procedures and are also suitable for conducting the hydroformylation reaction. In general, aprotic organic amides are useful solvents for the process of the present invention.

In the above-referred to copending application Ser. No. 290,622 it is stated that in the presence of certain amines, almost any solvent can be used, with description of various suitable solvents. If desired, amines and such solvents can be used in the present invention with acceptable reaction rates. However, amines tend to cause condensation of the glycol aldehyde product, and their use is unnecessary in the present invention in which good rates and catalyst stability are obtainable in amide solvents in the presence of certain substituted phosphines as described herein.

The hydroformylation processes of this invention are generally carried out at somewhat elevated pressures and temperatures, but in most instances relatively mild temperatures and pressures are not only desirable, but preferable. Generally higher pressures provide the best reaction rates and selectivity but very mild pressures may be used if optimum reaction rates and selectivity are not required. For example, pressures from 500 psi up to 6000 psi or higher can be used. Pressures in the range of 1000 to about 3000 psi are generally convenient. The processes are temperature dependent and it is generally desirable to use moderate temperatures of the order of 70° C. up to 150° C., and preferably from 90° C. up to 120° C.

The pressures referred to above are usually attained by the quantities of carbon monoxide and hydrogen charged to the reaction zone or system, which is normally provided by an autoclave or other pressure resistant vessel. While the CO and $H_2$ react in a 1:1 mole ratio in the hydroformylation process, it is not necessary to have them present in such ratio for the reaction. The CO and $H_2$ may conveniently be used in a mole ratio of about 1:1 as available in synthesis gas, but can also be employed in widely varying ranges, such as $CO:H_2$ mole ratios varying from about 10:90 to 90:10. Usually, however, it is desirable to employ $CO:H_2$ mole ratios in the range of about 4:1 to about 1:2, and to avoid large excesses of hydrogen thereby suppressing methanol production.

The formaldehyde emloyed in the processes can be utilized in any form which will generate formaldehyde under the reaction conditions. A preferred form of formaldehyde is paraformaldehyde.

The amount of catalyst employed in the hydroformylation processes herein does not appear to be critical and can vary considerably without adversely affecting the course of the reaction. In any event, the amount of catalyst used should be sufficient to catalyze the hydroformylation of formaldehyde with carbon monoxide and hydrogen to form glycol aldehyde, and, preferably, should be sufficient to achieve a reasonably practical reaction rate. Generally, the rhodium catalysts are used in amounts sufficient to provide at least about 0.001 gram atoms of rhodium, and up to about 0.09 gram atoms of rhodium, per liter of the reaction medium. The preferred amounts for most purposes are in the range of from about 0.003 to about 0.03 gram atoms per liter. The concentration of formaldehyde can vary widely, for example, from less than 0.1 mole per liter of reaction medium to over 3 moles per liter of reaction medium; concentrations in the range of about 1 mole to about 2 moles per liter may be convenient for use.

The present invention has the advantage of providing a process with good reaction rate and high selectivity to glycol aldehyde, which is conducted under conditions contributing to good catalyst stability. Rhodium catalysts in systems with little or no excess phosphine ligand give fairly good reaction rates, but tend to be unstable and lose activity. The presence of additional amounts of the usual phosphines improves the catalyst stability, but tends to lower the reaction rate and selectivity to glycol aldehyde. However, when the phosphine added in excess is a properly substituted phosphine as described herein, the desired catalyst stability is obtained, with retention of good reaction rate and selectivity to glycol aldehyde. Thus an excess of phosphine with electron-withdrawing aryl substitution can be employed and reaction rates can be obtained approaching or equal to those obtainable with a rhodium catalyst employing a triphenylphosphine to rhodium ratio of 2 or 3 to 1. Formaldehyde conversions of 75 to 80% or so can be obtained with reasonably short batch reaction times, along with conversions to glycol aldehyde of 85 to 90% or more. Correspondingly, condensation of the glycol aldehyde to other products is kept relatively low. The advantages of the use of properly substituted phosphines, as described herein, is particularly evident when a fairly high excess of phosphine is employed, as 5 or more moles of phosphine per rhodium atom.

The following specific examples are intended to illustrate the processes of this invention, but not to limit the scope thereof. In these examples the term "m mole" is intended to mean milli moles.

EXAMPLE 1

A 300 ml stainless steel autoclave equipped with a Magnedrive stirrer was charged with 0.0973 g of [Rh(CO)$_2$Cl]$_2$, (0.5 mmol Rh), 2.32 g tris-4-(trifluoromethylphenyl)phosphine, (5 mmol), 6.2 g paraformaldehyde (contains 97% formaldehyde, 0.2 mole) and 100 ml N,N-Dimethylacetamide (solvent). The reactor was then heated to 110° C. under 1800 psig CO:H$_2$(1:1). The reaction was run at 110° C. under 2500 psig total pressure for 1.5 hours. Analyses of the products indicated 79% conversion of formaldehyde. The selectivities were: 91% for glycolaldehyde; 2% for methanol; about 1% glyoxal; trace amount of glycerol; and about 6% C$_3$ and C$_4$ aldehydes and ketones (condensation products).

Upon substituting tris-(4-cyanophenyl) phosphine for the phosphine in the procedure of Example 1, and carrying out the procedure as described in Example 1, similar results, including high selectivity to glycolaldehyde, are to be expected.

EXAMPLE 2

The conditions were the same as Example 1 except that the amount of tris(4-trifluoromethylphenyl)phosphine was doubled. Analyses of the products after 2 hours of reaction indicated 77% conversion of formaldehyde. The selectivities were: 90% for glycolaldehyde; 2.6% methanol; 5% for C$_3$ and C$_4$ aldehydes and ketones. Small amounts of glyoxal and glycerol were also observed.

EXAMPLE 3

The conditions were the same as Example 1 except that the Rh complex charged was 0.345 g RhCl(CO)(PPh$_3$)$_2$, (0.5 mmol). Product analysis after 2 hours of reaction indicated 75% conversion of formaldehyde. The product selectivities were: 93% for glycolaldehyde; 3% for methanol; about 4% for C$_3$ and C$_4$ aldehydes and ketones.

EXAMPLE 4

(Comparison Example)

The conditions were the same as Example 1 except that the Rh complex charged was 0.345 g RhCl(CO)(PPh$_3$)$_2$, (0.5 mmol), and the phosphine was 3.7 g triphenylphosphine, (14 mmol). Product analysis after 2 hours of reaction indicated less than 44% conversion of formaldehyde. The selectivities for glycolaldehyde and methanol were 43% and 11%, respectively. the rest of the products were higher boiling byproducts.

EXAMPLE 5

(Comparison Example)

The conditions were the same as in Example 4 except that the added triphenylphosphine was 0.393 g. Product analysis after 2 hours of reaction indicated 65% conversion of formaldehyde. The selectivities for glycolaldehyde and methanol were 82% and 6%, respectively.

The tris(4-trifluoromethylphenyl) phosphine used in the above examples was prepared by reaction of p-bromobenzotrifluoride with magnesium to form a Grignard reagent, which was reacted with phosphorus trichloride; see G. R. Miller, A. W. Yankowsky, and S. O. Grim, J. Chem Physics, Vol. 51, 3185 (1969).

What we claim is:

1. The process of preparing glycol aldehyde which comprises reacting formaldehyde, carbon monoxide and hydrogen in the presence of rhodium catalyst and a triarylphosphine which is less basic than triphenyl phosphine and which has an electron-withdrawing substituent having a $\sigma_p^o$ value of at least 0.4 on an aryl ring, under conditions conducive to production of glycol aldehyde, including temperatures of about 70° to about 150° C., and pressures of about 500 psi up to about 6000 psi.

2. The process of claim 1 in which phosphine is present in excess of 3 mols per atom of rhodium.

3. The process of claim 1 in which phosphine having an electron-withdrawing substituent on an aryl ring is present in an amount of at least about 5 mols per atom of rhodium.

4. A process for the production of glycol aldehyde which comprises reacting carbon monoxide, hydrogen and formaldehyde in a solvent system at elevated temperature of about 70° to about 150° C. and elevated pressure in the presence of a rhodium catalyst effective to produce glycol aldehyde from such reactants, and having present a triaryl phosphine less basic than triphenylphosphine and in which there is a strongly electron-withdrawing group having a $\sigma_p^o$ value of at least 0.4 substituted on an aryl ring of the phosphine.

5. The process of claim 4 in which an organic amide solvent is employed.

6. The process of claim 5 in which the amide is an N,N-dialkylamide of a lower carboxylic acid.

7. The process of claim 4 in which the triarylphosphine is tris(4-trifluoromethylphenyl) phosphine.

8. The process of claim 4 in which an electron-withdrawing substituent is in para position.

9. The process of claim 4 in which an electron-withdrawing group is selected from trifluoromethyl, cyano, and nitro groups.

10. The process of claim 4 in which phosphine present is represented by $P(C_6H_4X)_3$ in which X is an electron withdrawing group with a value of at least 0.4.

11. The process of claim 10 in which X is trifluoromethyl.

12. The process of claim 4 in which carbon monoxide to hydrogen ratios are in the range of about 4:1 to about 1:2, temperatures are in the range of about 90° to about 120° C. and pressures are in the range of about 1000 to about 3000 psi.

13. The process of claim 12 in which a substituted triphenyl phosphine is present in which each phenyl group has an electron-withdrawing substituent in para-position to phosphorous, such substituent having a $\sigma_p^o$ value of at least 0.4.

14. The process of claim 13 which reaction is carried out in aprotic organic amide solvent employing the substituted triphenyl phosphine in amount in excess of 3 moles per atom of rhodium.

15. The process of claim 14 in which rhodium catalyst is present in an amount in the range of about 0.001 gram atom to about 0.09 gram atom per liter of reaction medium.

16. The process of claim 15 in which tris (4-trifluoromethylphenyl) phosphine is the substituted triphenylphosphine.

17. The process of claim 1 in which the triarylphosphine is tris(4-trifluoromethylphenyl) phosphine.

* * * * *